United States Patent [19]

Samson

[11] Patent Number: 5,505,725

[45] Date of Patent: Apr. 9, 1996

[54] SHAPEABLE OPTICAL FIBER APPARATUS

[75] Inventor: Gene Samson, Milpitas, Calif.

[73] Assignee: CardioGenesis Corporation, Santa Clara, Calif.

[21] Appl. No.: 379,002

[22] Filed: Jan. 27, 1995

Related U.S. Application Data

[63] Continuation of Ser. No. 873,964, Apr. 24, 1992, abandoned, which is a continuation of Ser. No. 605,774, Oct. 30, 1990, abandoned.

[51] Int. Cl.$^6$ ............................................ A61B 5/06
[52] U.S. Cl. ..................... 606/7; 606/10; 606/17; 607/89; 600/108; 604/95
[58] Field of Search ................. 128/4, 6; 606/7–19; 604/95; 607/88–93; 600/108

[56] References Cited

U.S. PATENT DOCUMENTS

| | | | |
|---|---|---|---|
| 4,662,368 | 5/1987 | Hussein et al. | 606/15 |
| 4,790,624 | 12/1988 | Van Hoye et al. | 128/45 M |
| 4,830,460 | 5/1989 | Goldenberg | 606/7 |
| 4,844,062 | 7/1989 | Wells | 606/7 |
| 4,913,142 | 4/1990 | Kittrell et al. | 606/15 |
| 5,019,040 | 5/1991 | Itaoka | 606/15 |

FOREIGN PATENT DOCUMENTS

| | | | |
|---|---|---|---|
| 2945080 | 5/1981 | Germany | 606/15 |
| 2147209 | 5/1985 | United Kingdom | 606/16 |

*Primary Examiner*—David M. Shay
*Attorney, Agent, or Firm*—Crosby, Heafey, Roach & May

[57] ABSTRACT

A shapeable optical fiber apparatus includes an optical fiber, a support structure secured over a distal end portion of the optical fiber, and terminates in a lens at its distal end. The transition area between the lens and optical fiber is reinforced with a sleeve that is adhesively bonded to the lens and fiber. The shapeable optical fiber apparatus may be carried within an inflatable balloon dilation catheter, which may be used for balloon angioplasty after a laser cutting procedure using the shapeable optical fiber apparatus to remove a portion of stenosis in the patient's vasculature.

11 Claims, 2 Drawing Sheets

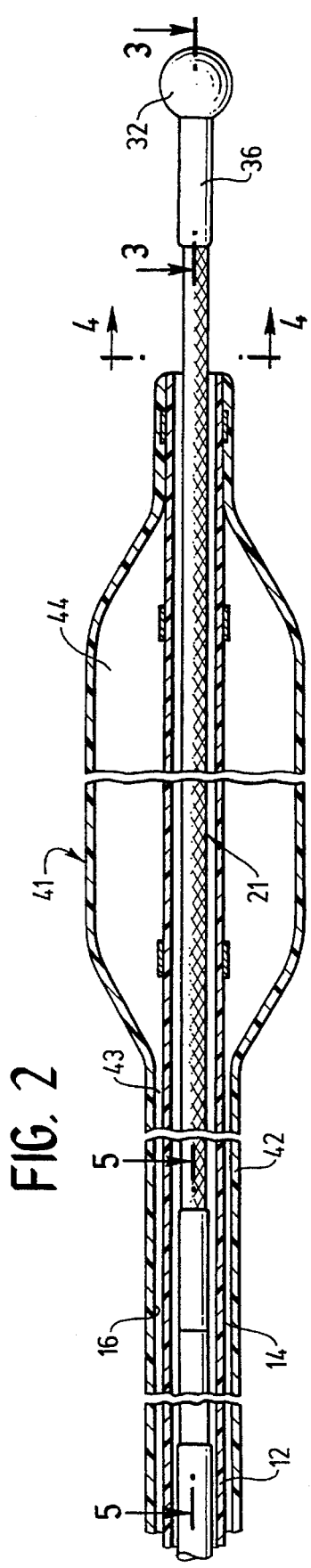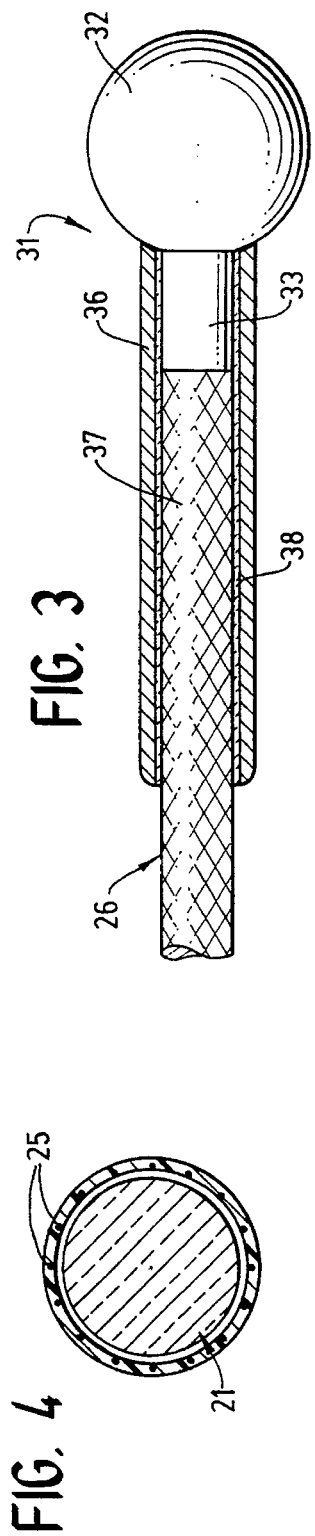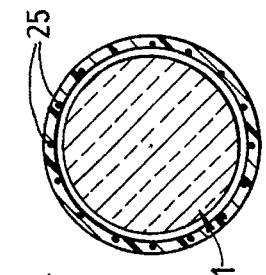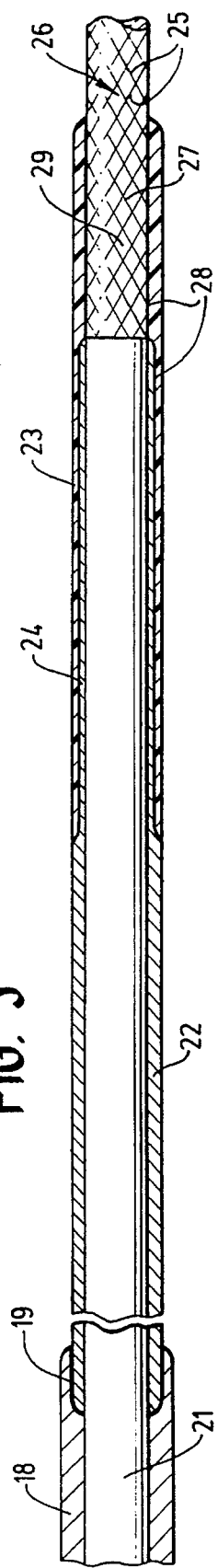

SHAPEABLE OPTICAL FIBER APPARATUS

This is a continuation of application Ser. No. 07/873,964, which was filed on Apr. 24, 1992, now abandoned, which is a continuation of application Ser. No. 07/605,774, filed Oct. 30, 1990 now abandoned.

FIELD OF THE INVENTION

This invention relates to optical fibers, and more particularly, relates to intravenous catheters including an optical fiber assembly.

BACKGROUND OF THE INVENTION

Laser catheter systems have been proposed which incorporate an optical fiber assembly to conduct laser energy from a remote location to the area to be lased through an otherwise conventional catheter. In one proposed application of such an apparatus, a laser angioplasty catheter houses an optical fiber for lasing a channel through an artery.

While such systems were initially believed to hold promise, they were later seen to have important limitations. Among these limitations was the inability to direct the energy to an exact location to be dissolved, with the result that damage could be sustained by the artery wall due to misdirected radiation. Additionally, the means of attaching the lens to the fiber had an important effect on the probability that the lens would become dislodged, damaged or misaligned from handling on its passage through the artery.

These same limitations were perceived to be important to other internal laser surgery systems, especially those which must be maneuvered within a patient's vasculature. These limitations are particularly important for systems which are not easily maneuvered by direct observations of the surgeon and which must therefore be capable of predictable direction through remote manipulation.

There remains, therefore, a need for a structure adaptable to a laser catheter system that allows the accurate direction of laser energy to a particular area and reduces the chance of damage to the patient from dislodging or disintegrating of the lens end of the optical fiber. It would also be beneficial if such a system could easily be combined with catheter configurations that could be used for a variety of procedures that incorporate the use of remotely directed laser energy.

Broadly, it is the object of the present invention to provide an improved optical fiber apparatus.

It is a further object of the present invention to provide an optical fiber apparatus which can direct laser radiation to a desired location.

It is a still further object of the present invention to provide an optical fiber apparatus which can be shaped into a desired configuration.

It is a yet further object of the present invention to provide an optical fiber apparatus which provides a strengthened attachment of a lens to an optical fiber.

These and other objects of the present invention will be apparent to those skilled in the art from the following detailed description of the invention and the accompanying drawings.

SUMMARY OF THE INVENTION

The present invention comprises a shapeable optical fiber apparatus. The optical fiber apparatus includes an optical fiber which has proximal and distal ends. Support means located intermediate the proximal and distal ends engage the exterior surface of the optical fiber over at least a portion of the length of the optical fiber. The support means comprises a rigid deformable structure which is coextensive with the exterior surface of that portion of the optical fiber. The support means allows the optical fiber to be shaped and supported in a desired configuration. In one preferred embodiment, the support means comprises a tubular sleeve, preferably a tungsten wire braid.

BRIEF DESCRIPTION OF THE DRAWINGS

FIG. 2 is an enlarged cross-sectional view of the distal portion of the shapeable optical fiber assembly in the distal extremity of the catheter shown in FIG. 1.

FIG. 3 is an enlarged longitudinal cross-sectional view taken along the line 3—3 of FIG. 2.

FIG. 4 is an enlarged transverse cross-sectional view of the distal portion of the optical fiber assembly taken along line 4—4 in FIG. 2.

FIG. 5 is an enlarged longitudinal sectional view of a proximal portion of the optical fiber assembly, taken along line 5—5 of FIG. 2.

DETAILED DESCRIPTION OF THE PREFERRED EMBODIMENT

Figure 1:
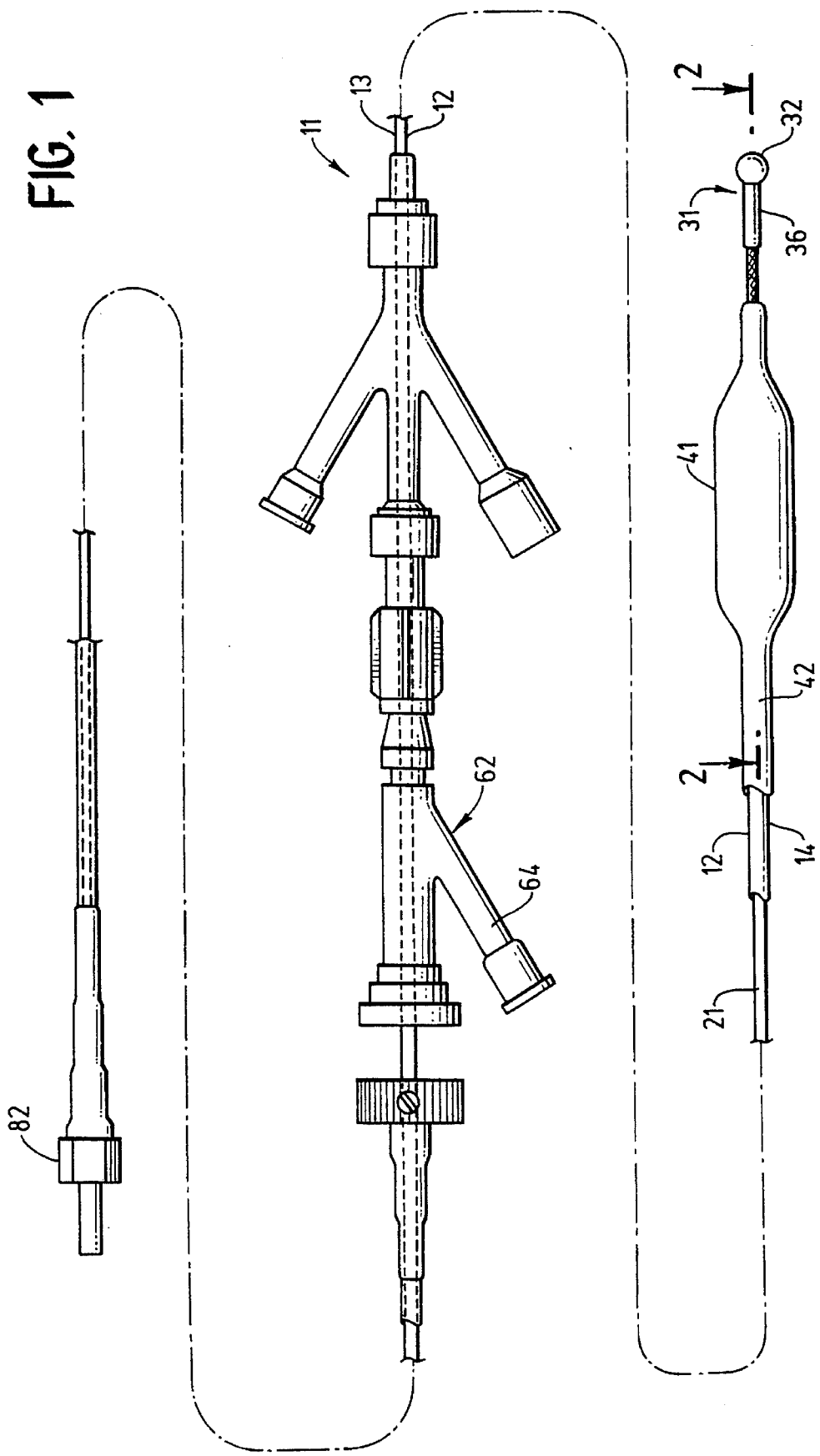
FIG. 1 is a side elevational view of a balloon dilatation catheter with laser cutting capabilities incorporating the shapeable optical fiber assembly of the present invention.

In general, the shapeable optical fiber apparatus according to the present invention includes an optical fiber having a support means secured to at least a portion of the optical fiber, and is preferably secured to a distal portion of the optical fiber. In the preferred embodiment, the shapeable optical fiber is disposed within a tubular member such as a dilation catheter, having an inflatable balloon carried by the distal extremity of the tubular member. The apparatus would then also include a lens tip secured to the distal extremity of the optical fiber. A reinforcing collar encloses the distal end of the optical fiber, abuts the lens at the collar's distal end, and is adhesively attached to the lens and the fiber.

The manner in which the present invention provides its advantages may be more easily understood with reference to FIG. 1. An intravenous catheter 11 includes an elongate flexible tubular member 12 having proximal portion 13 and distal portion 14. Tubular member 12 can be formed of a suitable material such as polyethylene tubing, and can be of various sizes depending on the size of the vessel it is desired to negotiate with the catheter. By way of example, tubular member 12 can have an outside diameter of 0.050 inches and an inside diameter of 0.040 inches.

The preferred embodiment of the present invention is illustrated in FIG. 2. Tubular member 12 is provided with a lumen 16 extending the length thereof. The shapeable optical fiber element or assembly 21 is preferably adapted to extend through lumen 16 so that optical fiber element 21 may be used intravenously. Optical fiber element 21 typically may have a diameter of approximately 200 microns, and a length of approximately 400 cm.

The manner in which optical fiber element 21 is reinforced to give additional rigidity and to enhance its pushability is illustrated in FIG. 5. A proximal portion of optical fiber element 21 is currently preferably disposed within a first metallic hypotube 18, preferably formed of stainless steel, or another similar suitable material. First hypotube 18 typically has an inside diameter of about 0.020 inches, and an outside diameter of about 0.032 inches, and may have a suitable length, such as about 10 cm.

A second, narrower metallic hypotube 22, also preferably formed of stainless steel or another suitable material, is disposed within a distal portion of first hypotube 18 and is secured thereto, preferably with epoxy adhesive 19. Optical fiber element 21 is disposed within second hypotube 22, which typically may extend about 125 cm. Second hypotube 22 typically has an inside diameter of about 0.011 inches, and an outside diameter of about 0.018 inches, except that the distal 5 cm of the second hypotube is ground cut to have an outside diameter of about 0.015 inches.

A polyamide tube 23 extends over the ground cut distal portion 24 of second hypotube 22, beyond the distal end of second hypotube 22 and over a portion of the distal extremity 29 of optical fiber element 21 for about 2 cm. Polyamide tube 23 is secured to second hypotube 22 and to the distal extremity 29 of optical fiber element 21 by epoxy adhesive 28. The stepped reduction of diameter of the hypotubes from proximal portion 13 to distal portion 14 of optical fiber element 21 provides for appropriate gradations of support and enhanced pushability along the length of optical fiber element 21.

The preferred embodiment is further illustrated in FIGS. 3–5. The preferred embodiment provides shapeability to the distal extremity 29 of optical fiber element 21 through a support means 26. Support means 26 may be implemented as a metallic braid formed of coils 25 of tungsten wire or another suitable material about 0.001 inches in diameter. Support means 26 is secured over at least a portion of optical fiber element 21. Support means 26 is preferably secured to optical fiber element 21 by adhesive such as epoxy, but other methods of securing will be apparent to those skilled in the art. Support means 26 is preferably secured over the distal extremity 29 of optical fiber element 21 from the distal end of second hypotube 22 to approximately the lens portion 31 of optical fiber element 21.

The proximal portion 27 of support means 26 is also preferably secured within the distal portion of polyamide tube 23 by epoxy adhesive 28, preferably of the type marketed as FDA-2 by TRACON. The tungsten braid has excellent shape memory, radiopacity, and high strength. The braid may have an outer diameter of about 0.015 inches, and may be approximately 30–40 cm, for example, or various lengths to enhance shapeability. The braid may thus be shaped and reshaped many times. Without the adhesive bonding of the braid to the optical fiber the braid remains generally flexible, and may not have sufficient shape memory.

In the preferred embodiment of the present invention, a lens assembly 31 may also be provided secured to the distal extremity 29 of optical fiber element 21. The lens assembly may be of any suitable construction, depending upon the specific application for which the apparatus of the present invention is to be used. In the drawings, lens assembly 31 shown for illustrative purposes includes a ball lens 32 formed of a suitable material such as silica, which is bonded to a silica stem 33 having a matched index of refraction.

Optical fiber assembly 21 may also incorporate a tubular reinforcing sleeve 36 to reinforce the juncture between ball lens 32 and the optical fiber. Tubular sleeve 36 preferably is a hollow, essentially cylindrical member that is beveled at the distal end to mate with the proximal end of ball lens 32. Epoxy material 38 is placed in the area between tubular sleeve 36, ball lens 32 and the optical fiber to adhesively bond them together. In practice, it has been found that it is advantageous to fabricate tubular sleeve 36 of 304 Stainless Steel and to utilize TRICON FDA-2 epoxy as an adhesive.

Since radiation from optical fiber element 21 is primarily concentrated in a small angle in front of the distal end of ball lens 32, relatively small amounts of energy impinge upon tubular sleeve 36. Thus there is a relatively little heating of tubular sleeve 36 by energy transmitted through the fiber. This reduces the chance that there will be a degradation of the adhesive between tubular sleeve 36 and ball lens 32.

Tubular sleeve 36 extends over stem 33 and typically may have an inside diameter of 0.016 inches and an outside diameter of 0.028 inches. Tubular sleeve 36 extends to ball lens 32 and is bonded to the distal extremity 37 of support means 26 by suitable means such as an epoxy 38 which extends inside the sleeve. Stem 33 is secured to the distal extremity 29 of optical fiber element 21.

A suitable coating such as a polyamide coating can be applied to the exterior surface of tubular sleeve 36. Similarly, a suitable coating such as polyamide may be used to recoat the fiber-lens interface area after fusing of the lens to the fiber, which destroys the original polyamide coating on the fiber.

Ball lens 32 can have a suitable diameter as, for example, 1.0 mm. However, it should be appreciated that, if desired, larger lenses can be utilized. Ball lens 32 can, if desired, have a diameter which is larger than the inside diameter of tubular member 12, which is the diameter of lumen 16. This makes optical fiber assembly 21 non-removable from tubular member 12.

In a preferred embodiment, an inflatable balloon 41 is also carried by the distal extremity 14 of elongate flexible tubular member 12. Balloon 41 as shown can be formed integrally with an elongate flexible tubular member 42 which extends coaxially of elongate flexible tubular member 12. Balloon 41 can, if desired, be formed as a separate element and bonded to tubular member 42.

An annular flow passage 43 is formed between tubular member 12 and tubular member 42. Annular flow passage 43 is in communication with the interior 44 of balloon 41 so that balloon 41 can be inflated and deflated. Balloon 41 is inflated by introducing a balloon inflation medium through annular flow passage 43 and is deflated by withdrawing the same through annular flow passage 43.

Operation and use of the preferred embodiment of the present invention may now be briefly described. The shapeable optical fiber assembly is disposed within a balloon dilatation catheter 11. The distal portion 29 of optical fiber element 21 is preferably shaped as desired. A guiding catheter (not shown) is then inserted into the vessel of the patient to be utilized for guiding catheter 11. Thereafter catheter 11 can be inserted into the guiding catheter, and catheter 11 can be advanced so that he balloon 41 is within a stenosis. In this manner, the device may be used without a guidewire, with the lens tip 31 and shapeable portion of the catheter combining to provide the necessary mechanical characteristics used to guide catheter 11 to an area of stenosis.

Ball lens 32 is self guiding and greatly reduces possible perforation of the side wall of the vessel being negotiated. Optical fiber assembly 21 with its ball lens 32 facilitates negotiation of tortuous vessels. Laser energy can then be introduced by a laser (not shown) connected to an SMA connector 82 causing an appropriate amount of energy to be directed down the optical fiber assembly 21 and into ball lens 32 to cause ablation of the atheromatous tissue in the stenosis while at the same time minimizing adjacent thermal injury to the vessel. During this procedure, the tissue being irradiated can be immersed in a suitable saline solution by introducing the saline solution into a side arm 64 of a two arm adapter 62.

Alternatively, the laser irradiation may occur in the presence of blood in the region adjacent ball lens 32. This can occur because one advantage of the present invention is that the radiation pattern of the lens, which is concentrated in the immediate distal area of the lens concentric with the lens, does not have to be actively aimed and may be placed in close contact with the stenosis to be removed. Thus, there is very little blood between the lens and the stenosis to be irradiated by laser energy and absorb the energy emitted.

It should be noted that the shapeable optical fiber apparatus may be used apart from a balloon dilation catheter, and may be guided for use in laser surgery or other methods of treatment or diagnosis by other means, such as by a guiding catheter, for example.

While particular forms of invention have been illustrated and described, it will be apparent that various modifications can be made without departing from the spirit and scope of the invention. Accordingly, it is not intended that the invention be limited, except as by the appended claims.

What is claimed is:

1. A catheter assembly for delivery of laser energy comprising:
   a) an elongated catheter with proximal and distal ends and an inner lumen extending therein;
   b) disposed within the inner lumen of the elongated catheter a shapable optical fiber which has proximal and distal ends, a distal extremity proximal to the distal end having an exterior surface, and means for shaping and supporting the distal extremity of the optical fiber in a desired configuration which includes a longitudinally deformable tubular structure coaxially surrounding and secured to the exterior surface of the distal extremity.

2. The catheter assembly of claim 1 wherein said tubular structure surrounding and secured to the distal extremity of the optical fiber has a distal end disposed within a metallic tube.

3. The catheter assembly of claim 1 wherein the tubular support structure is secured to the exterior of the optical fiber by epoxy adhesive.

4. The catheter assembly of claim 1 wherein metallic tubing is disposed about the optical fiber proximal to the tubular structure surrounding and secured to the distal extremity of the optical fiber.

5. The catheter assembly of claim 1, wherein a proximal portion of said optical fiber is disposed within a tubular member and said tubular structure surrounding and secured to the distal extremity of the optical fiber is secured to said tubular member.

6. The apparatus of claim 5, further comprising a flexible balloon dilatation catheter, at least a portion of said tubular member and at least a portion of said support means being disposed within said flexible elongated balloon dilatation catheter.

7. The catheter assembly of claim 1 including lens means secured to the distal end of the optical fiber to collect radiation emitted from the distal end of the optical fiber and direct collected radiation to a location spaced distally of the lens means.

8. The catheter assembly of claim 7, wherein said tubular structure surrounding and secured to the distal extremity of the optical fiber is secured to said lens means at said distal end of said optical fiber.

9. The catheter assembly of claim 1 wherein the tubular structure surrounding and secured to the distal extremity is formed of braided wire.

10. The catheter assembly of claim 9 wherein the braided wire is formed of tungsten.

11. The apparatus of claim 10, wherein said braid is formed from two intertwined coils of tungsten wire coiled in opposite directions.

* * * * *